United States Patent
Wei et al.

(10) Patent No.: US 9,822,136 B2
(45) Date of Patent: Nov. 21, 2017

(54) CHEMICAL INHIBITORS OF SEBOCYTE FUNCTION

(71) Applicants: Edward T. Wei, Berkeley, CA (US); Seong J. Kim, Los Alamitos, CA (US)

(72) Inventors: Edward T. Wei, Berkeley, CA (US); Seong J. Kim, Los Alamitos, CA (US)

(*) Notice: Subject to any disclaimer, the term of this patent is extended or adjusted under 35 U.S.C. 154(b) by 0 days.

(21) Appl. No.: 14/998,864

(22) Filed: Feb. 23, 2016

(65) Prior Publication Data
US 2017/0240575 A1  Aug. 24, 2017

(51) Int. Cl.
| | |
|---|---|
| *A61Q 19/00* | (2006.01) |
| *A61K 8/55* | (2006.01) |
| *A61K 31/683* | (2006.01) |
| *C07F 9/53* | (2006.01) |
| *A61K 9/00* | (2006.01) |

(52) U.S. Cl.
CPC .............. *C07F 9/5304* (2013.01); *A61K 8/55* (2013.01); *A61K 9/0014* (2013.01); *A61K 31/683* (2013.01); *A61Q 19/00* (2013.01); *A61Q 19/008* (2013.01); *A61K 2800/244* (2013.01)

(58) Field of Classification Search
CPC ........ A61K 9/0014; A61K 8/55; A61Q 19/00; A61Q 19/008; C07F 9/5304
See application file for complete search history.

(56) References Cited

U.S. PATENT DOCUMENTS

| | | | | |
|---|---|---|---|---|
| 3,331,878 | A * | 7/1967 | Hill | C07F 9/53 510/236 |
| 4,070,496 | A * | 1/1978 | Rowsell | A24B 15/30 131/276 |
| 2002/0119109 | A1* | 8/2002 | Herpens | A61K 8/26 424/68 |
| 2015/0164924 | A1* | 6/2015 | Wei | C07F 9/532 424/443 |

* cited by examiner

*Primary Examiner* — Theodore R. West

(57) ABSTRACT

The present discovery pertains to the discovery of certain amphiphilic compounds that may be useful for the management of sebum secretion in subjects with acne, oily skin, or seborrheic dermatitis. These compounds are 1-dialkylphosphorylalkanes with the longest alkyl group being seven or more carbons. Preferably, a compound is dissolved in a dermatologically acceptable vehicle, and delivered to the skin in a solution, gel, lotion, cream, or ointment. The method of application may be with the surface of the finger, or via an applicator. The decrease is sebum secretion in certain subjects may result in skin conditions that enhance cosmetic appearance and ameliorate skin disorders.

15 Claims, 7 Drawing Sheets

CHEMICAL INHIBITORS OF SEBOCYTE FUNCTION

BACKGROUND OF THE INVENTION

Technical field

The present discovery pertains generally to the field of cosmetic and therapeutic compounds. More specifically the invention pertains to certain 1-dialkylphosphorylalkanes, as described herein as "Dapa compounds" that are useful, for example, in the treatment of disorders (e.g., diseases) of sebocyte function, including: acne, seborrheic dermatitis, and "oily skin", and other disorders of cellular proliferation. The present invention also pertains to topical dermatological compositions formulated to deliver the Dapa compounds, and the use of such compounds and compositions, for example, in cosmetic therapy or in dermatological therapy.

Description of Related Art

Rowsell and Spring [Phosphine oxides having a physiological cooling effect. U.S. Pat. No. 4,070,496. 1978] described trialkylphosphine oxides to have a "physiological cooling action".

The pilosebaceous unit [PSU] is an epidermal invagination found on most surfaces of the human body and consists of a hair follicle, a sebaceous gland, and an arrector pili muscle. The sebaceous glands produce an oily/waxy substance called sebum which is extruded into the hair follicle and then onto the surface of the skin. The PSU is distributed throughout the skin except for the palms and soles, and the density of PSU is especially high in the scalp, face, and upper body. Sebaceous glands are also found in non-haired areas [glabrous skin] of eyelids, nose, penis, labia minora and nipples [Hinde. et al. A practical guide for the study of human and murine sebaceous glands in situ. Exp. Dermatol. 22, 631-7 (2013)].

The principal cell of the sebaceous gland is the sebocyte. When sebocytes mature and burst [holocrine secretion], the cell constituents form sebum which is mostly lipids such as triglycerides, free fatty acids, wax esters, squalene, and cholesterol and cholesterol esters, and other cellular products [Picardo et al. Sebaceous gland lipids. Dermatoendocrinol. 1, 68-71 (2009)]. The sebum protects the skin against excessive hydration and helps regulate body temperature.

Sebum dysfunction is associated with acne, oily skin, and skin disorders such as seborrheic dermatitis [Zouboulis. Acne and sebaceous gland function. Clin. Dermatol. 22, 360-6 (2004)]. These conditions have a high prevalence [e.g. for acne, ~14 million office visits per year in the US; for oily skin a ~26% prevalence in Chinese women, confirmed by Sebumeter® measurements] and are associated with a perceived decrease in quality of life [Nouveau-Richard et al. Oily skin: specific features in Chinese women. Skin research and technology: 13, 43-8 (2007); Wu et al. A preliminary investigation of the impact of oily skin on quality of life and concordance of self-perceived skin oiliness and skin surface lipids (sebum). Int. J. Cosmet. Sci. 35, 442-7 (2013)]. Currently, the only drugs that directly target sebocyte function are the androgen receptor antagonists, e.g. cyproterone acetate, and possibly isotretinoin. Antagonists of melanocortin receptor 5 have been proposed, but have not yet reached the clinic [Zhang et al. Melanocortin-5 receptor and sebogenesis. Eur. J. Pharmacol. 660, 202-6 (2011)].

Acne, oily skin, and seborrheic dermatitis affect the appearance of the facial skin and are a source of embarrassment and distress. The major pathogenic factor promoting acne is increased sebum production from the pilosebaceous unit [PSU] caused by androgen action on seboycytes. Other factors in pathogenesis are ductal hypercornification, colonization of the PSU by Propionibacterium acnes, and inflammation [Cunliffe et al. Comedone formation: etiology, clinical presentation, and treatment. Clin. Dermatol. 22, 367-74 (2004)]. Oily skin [seborrhea] is a common cosmetic problem that occurs when oversized sebaceous glands produce excessive amounts of sebum giving the appearance of shiny and greasy skin. Seborrheic dermatitis is characterized by red, flaking, greasy areas of skin, most commonly on the scalp, nasolabial folds, ears, eyebrows and chest. The prevalence of seborrheic dermatitis is not precise but may affect up to 1 to 5% of the adult population [Schwartz et al. Seborrheic dermatitis: an overview. Am. Fam. Physician 74, 125-30 (2006)].

A therapeutic agent that interferes with sebocyte function and reduce sebum secretion will have benefits in disorders of sebum function such as acne, oily skin, and seborrheic dermatitis.

BRIEF SUMMARY OF THE INVENTION

A decrease in sebum secretion [measured with a Sebumeter®] from the forehead skin of human subjects after application of certain 1-dialkylphosphorylalkanes (a herein referred sometimes as "Dapa") is described hereinafter. The mechanisms of actions of Dapa agents were then examined on cultured human sebocytes. Surprisingly, some of the Dapa showed a potent inhibitory effect on sebocyte function. For one Dapa compound [1-12] the inhibitory effects on sebocyte function were observed at less than 30 µg/mL. It is noted that the amphiphilic characteristics of the Dapa enhance potency. The exact cellular targets that mediate these effects have not yet been characterized, but these Dapa chemicals, formulated for delivery to the skin, are believed useful in modulating disorders related to sebum secretion and for other disorders of lipid synthesis and cellular proliferation.

DETAILED DESCRIPTION OF THE INVENTION

Figure 1:
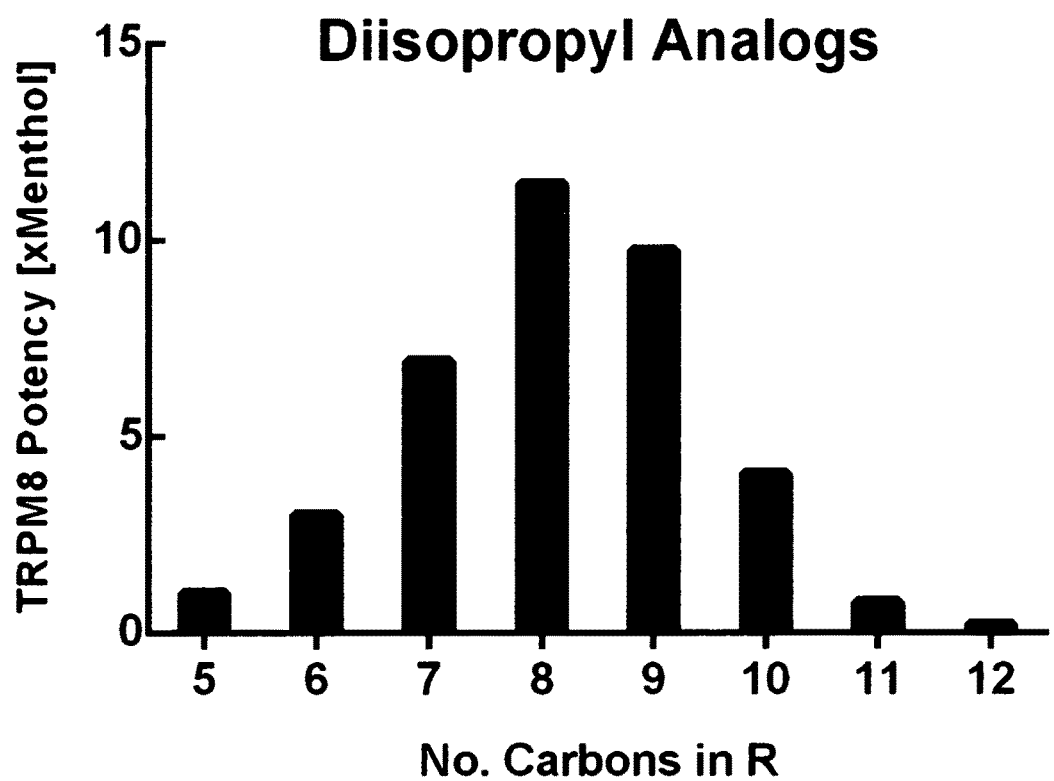
FIG. 1. is a graph showing the potencies of 1-diisopropylalkanes on the TRPM8 receptor assay. On the ordinate, potency is shown relative to l-menthol. On the abscissa, the number of carbons in the n-alkane is enumerated.

Selected chemical agents, called Dapa compounds, were synthesized and examined for cooling actions on the skin and for activities on the ion channel called TRPM8. It was noted that two analogs, 1-7 and 1-8, applied to the forehead skin, at a concentration of 20 mg/mL and a volume of 0.08 to 0.15 mL, did not change skin temperatures but elicited robust localized cooling and refreshing sensations that lasted for several hours. The skin felt fresh, dry, and cool. Skin temperature after application of 1-7 was measured and found to be unchanged. It was noted that sebum secretion of the forehead skin in human subjects was inhibited by topical application of 1-7. The anti-seborrheic properties of 1-7 and 1-8 were then examined in the laboratory on isolated sebocytes in culture. 1-8 was found to be active for inhibiting sebocyte viability and sebum synthesis. Dapa compounds [and others] were then screened on sebocytes using cell viability (MU assay) and $^3$H-thymidine incorporation as indices of sebocyte function. Surprisingly, compounds 1-10, 1-11, and 1-12 were found to have potent inhibitory activity on sebocyte function. For example, the synthesis of squalene, a lipid characteristic of skin cells, was strongly inhibited by 1-12. The 1-10, 1-11, and 1-12 compounds have low potency on TRPM8: hence their activities on sebocytes were not related to the TRPM8 receptor. Further examination of the chemical structures of 1-10, 1-11, and 1-12 suggest that the non-ionic amphiphilic characteristics of these molecules confer sebocyte-inhibitory activities, with the longer chain alkane selectively making the molecule more potent. Thus, a set of compounds with a new mechanism of action for reducing sebum production is identified. In the sections below, these observations are described in detail.

In summary, several Dapa agents were found to have potent [submicromolar] inhibitory effects on human sebocyte functions in culture. One of the Dapa-compounds, coded 1-12, was active at 30 μg/mL. This potent activity was unexpected and 1-12 likely can be utilized to ameliorate "oily skin", acne, and seborrheic dermatitis. Such direct drug actions on human sebocytes have not been described previously. Preferred embodiments are believed useful in treating disorders of sebaceous gland function, and in other conditions of cellular proliferation and lipid synthesis.

EXAMPLES

Study 1. Chemical Synthesis and TRPM8 Activity

The present invention pertains to certain 1-dialkylphosphorylalkanes described herein as "Dapa compounds". As noted earlier, Rowse!! and Spring [Phosphine oxides having a physiological cooling effect. U.S. Pat. No. 4,070,496. 1978] described trialkylphosphine oxides to have a "physiological cooling action". Dimethyl- and diethyl-phosphorylalkanes have been synthesized and evaluated for physical chemical properties associated with micelle formation by Lunkenheimer et al. [On the adsorption properties of surface chemically pure aqueous solutions of n-alkyl-dimethyl and n-alkyl-diethyl phosphine oxide, Colloids and Surfaces 22, 215-224 (1987)].

The Dapa compounds of importance here have this general chemical structure:

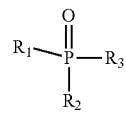

where $R_1$ and $R_2$ are isopropyl, or n-propyl, and $R_3$ is an alkyl chain of 10 to 18 carbons.

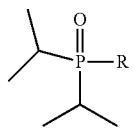

The preferred embodiments for inhibition of sebocyte function are where $R_1$ and $R_2$ are isopropyl. Thus, the preferred embodiments are the 1-diisopropylphosphorylalkanes where R =n-decanyl, n-undecanyl, and n-dodecanyl.

"Dapa" is an abbreviation for 1-dialkylphosphorylalkanes. Other synonyms for this chemical group include: trialkylphosphine oxides or 1-dialkylphosphinoylalkanes. The phosphorus is pentavalent in Dapa. The third alkyl group, $R_3$, in the general formula may be numbered from 4 to 12, corresponding to the butyl, pentyl, hexyl, heptyl, octyl, nonyl, decanyl, undecanyl and dodecanyl sidechain, respectively. The $R_3$ alkanes are linear or "normal" in configuration, with the phosphoryl group attached to the primary position of the carbon chain. Individual compounds in Table 1 and 2 are labelled as "1-x" for the diisopropyl series or "2-x" for the disec-butyl series, wherein x is a numerical identifier of the number of carbons in $R_3$. Hence, 1-7, 1-8, and 1-12 are 1-diisopropylphosphorylheptane, 1-diisopropylphosphoryloctane, and 1-diisopropylphosphoryldodecane, respectively, and 2-6 and 2-7 are 1-disec-butylphosphorylhexane and 1-disec-butylphosphorylheptane, respectively.

The Dapa compounds were synthesized by the following general method: 100 mL (23.7 g, ~200 mmol) of isopropylmagnesium chloride (or, separately, sec-butylmagnesium chloride in the case of the disec-butyl derivatives) were obtained from Acros, as a 25% solution in tetrahydrofuran (THF), and placed under nitrogen in a 500 mL flask (with a stir bar). Diethylphosphite solution in THF (from Aldrich, D99234; 8.25 g, 60.6 mmol in 50 mL) was added drop-wise. After approximately 30 min, the reaction mixture warmed up to boiling. The reaction mixture was stirred for an extra 30 min, followed by a drop-wise addition of the appropriate n-alkyl iodide solution in THF (from TCI; 60 mmol in 20 mL). The reactive mixture was then stirred overnight at room temperature. The reaction mixture was diluted with water, transferred to a separatory funnel, acidified with acetic acid (~10 mL), and extracted twice with ether. The ether layer was washed with water and evaporated (RotaVap Buchi, bath temperature 40° C.). The light brown oil was distilled under high vacuum. The final products, verified by mass spectrometry, were transparent liquids that were colorless or slightly pale yellow. Table 1 and 2 list some of the Dapa compounds that were synthesized and tested.

The in vitro effects of test articles were first evaluated on cloned hTRPM8 channel. Test compounds were sent to ChanTest Corporation (14656 Neo Parkway, Cleveland, Ohio 44128, USA) for assay. The test cells were Chinese Hamster Ovary (CHO) cells stably transfected with human TRPM8 cDNAs. Test solutions, and the L-menthol reference, were prepared by diluting stock solutions in HEPES-buffered physiological saline (HBPS). Substances were evaluated at 8 concentrations (0.03 to 300 μM) with n=4 replicates per determination. For Fluorescence Imaging Plate Reader (FLIPRTETRAT") assay, cells were plated in 384-well black wall, flat clear-bottom microtiter plates (Type: BD Biocoat Poly-D-Lysine Multiwell Cell Culture Plate) at approximately 30,000 cells per well. Cells were incubated at 37° C. overnight to reach a near confluent monolayer appropriate for use in a fluorescence assay. The test procedure was to remove the growth media and to add 40 μL of HBPS containing Fluo-8 for 30 minutes at 37° C. 10 μL of test compound, vehicle, or control solutions in HBPS were then added to each well and read for 4 min using a Fluo-8 calcium kit and the FLIPRTETRAT" instrument (Molecular Devices, Sunnyvale, California). Subsequently, compounds were tested by David Andersson at King's College, London, U.K. using standard published procedures [Andersson et al. TRPM8 activation by menthol, icilin, and cold is differentially modulated by intracellular pH. J. Neurosci. 24, 5364-9 (2004)].

Concentration-response data were analysed via the FLIPR Control software that is supplied with the FLIPR System (MDS-AT) and fitted to a Hill equation of the following form: Response=Base+(Max−Base)/1+(xhalf/x)$^{rate}$, where: "Base" is the response at low concentrations of test compound; "Max" is the maximum response at high concentrations; "xhalf" is the $EC_{50}$ (the concentration of test compound producing half-maximal activation); and "rate" is the Hill coefficient. Nonlinear least squares fits were made assuming a simple one-to-one binding model. The same data set was further analysed using GraphPad Prism 6 software (San Diego, Calif.) to obtain the 95% Confidence Intervals.

Table 1 and Table 2 show the structures of compounds that were tested on TRPM8 activation. The results for the tests are shown in Table 3 and FIG. 1. It can be seen that the more potent compounds are 1-7, 1-8, and 1-9 for the diisopropyl series and 2-6, and 2-7 for the disec-butyl series. 1-12 has very low activity on TRPM8.

FIG. 1. is a graph showing the potencies of 1-diisopropylalkanes on the TRPM8 receptor assay. On the ordinate, potency is shown relative to I-menthol. On the abscissa, the number of carbons in the n-alkane is enumerated.

TABLE 1

Compounds tested on TRPM8 activation, skin, and sebocytes.

| Code | R or $R_3$ | Chemical Name | Structure |
|---|---|---|---|
| 1-5 | n-$C_5H_{13}$ | 1-diisopropylphosphorylpentane | 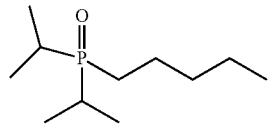 |
| 1-6 | n-$C_6H_{13}$ | 1-diisopropylphosphorylhexane | 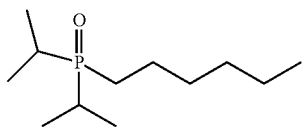 |
| 1-7 | n-$C_7H_{15}$ | 1-diisopropylphosphorylheptane | 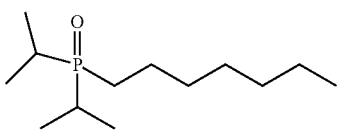 |
| 1-8 | n-$C_8H_{17}$ | 1-diisopropylphosphoryloctane | 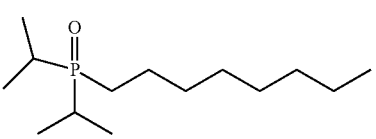 [SMILES: CCCCCCCCP(=O)(C(C)C)C(C)C] |
| 1-9 | n-$C_9H_{19}$ | 1-diisopropylphosphorylnonane | 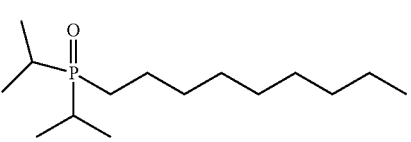 [SMILES: CCCCCCCCCP(=O)(C(C)C)C(C)C] |
| 1-10 | n-$C_{10}H_{21}$ | 1-diisopropylphosphoryldecane | 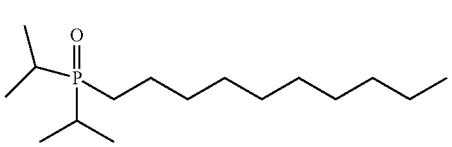 [SMILES: CCCCCCCCCCP(=O)(C(C)C)C(C)C] |

TABLE 1-continued

Compounds tested on TRPM8 activation, skin, and sebocytes.

| Code | R or $R_3$ | Chemical Name | Structure |
|---|---|---|---|
| 1-11 | n-$C_{11}H_{23}$ | 1-diisopropylphosphorylundecane | 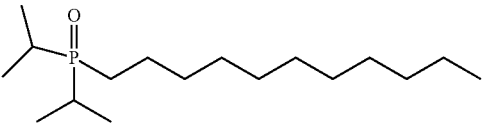 [SMILES: CCCCCCCCCCCP(=O)(C(C)C)C(C)C] |
| 1-12 | n-$C_{12}H_{25}$ | 1-diisopropylphosphoryldodecane | 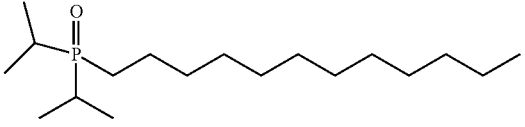 [SMILES: CCCCCCCCCCCCP(=O)(C(C)C)C(C)C] |

TABLE 2

Compounds tested on TRPM8 activation, skin, and sebocytes.

| Code | R or $R_3$ | Chemical Name | Structure |
|---|---|---|---|
| 2-4 | n-$C_4H_9$ | 1-disec-butylphosphorylbutane | 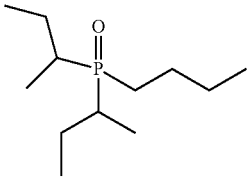 |
| 2-5 | n-$C_5H_{11}$ | 1-disec-butylphosphorylpentane | 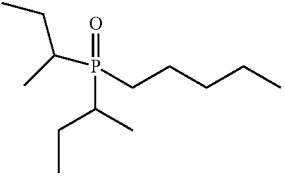 |
| 2-6 | n-$C_6H_{13}$ | 1-disec-butylphosphorylhexane | 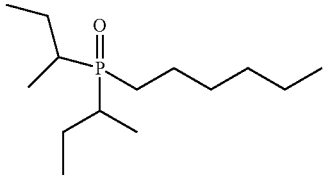 [SMILES: CCCCCCP(=O)(C(C)CC)C(C)CC] |
| 2-7 | n-$C_7H_{15}$ | 1-disec-butylphosphorylheptane | 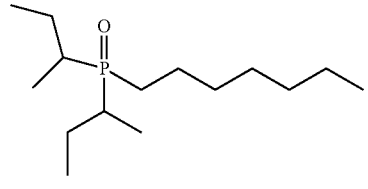 [SMILES: CCCCCCCP(=O)(C(C)CC)C(C)CC] |
| 2-8 | n-$C_8H_{17}$ | 1-disec-butylphosphoryloctane | 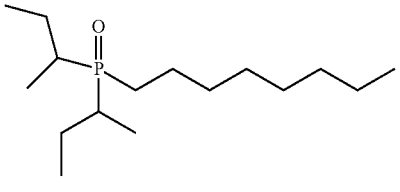 [SMILES: CCCCCCCCP(=O)(C(C)CC)C(C)CC] |

TABLE 3

EC$_{50}$ on TRPM8 and relative potency to I-menthol.

| Code | EC$_{50}$ μM | 95% Confidence Interval | Relative Potency |
|---|---|---|---|
| I-Menthol | 3.8 | 2.5 to 5.6 | 1.0 |
| 1-5 | 5.6 | 4.4 to 7.2 | 0.7 |
| 1-6 | 2.4 | 1.5 to 4.0 | 1.6 |
| 1-7 | 0.7 | 0.5 to 1.0 | 5.4 |
| 1-8 | 0.7 | 0.5 to 1.0 | 5.4 |
| 1-9 | 0.9 | 0.4 to 2.5 | 4.0 |
| 2-4 | 14.5 | 7 to 29 | 0.3 |
| 2-5 | 1.7 | 1.0 to 2.9 | 2.2 |
| 2-6 | 0.8 | 0.5 to 1.3 | 4.7 |
| 2-7 | 1.1 | 0.6 to 2.3 | 3.4 |
| 2-8 | 1.3 | 0.7 to 2.3 | 2.9 |

Study 2: Cooling on Skin, Tissue Temperatures, and Sebum Secretion

When certain Dapa compounds are applied to the zygomatic and forehead skin, sensations of coolness/cold are felt and can be graded in intensity [Wei. 1-Di-isopropyl-phosphinoyl-alkanes as topical agents for the treatment of sensory discomfort. US 2015/0164924]. For example, one can rate the sensation as 0, 1, 2, or 3 with: 0 as no change; 1 as slight coolness, or cold; 2 as clear-cut signal of coolness or cold; and 3 as strong cooling or cold. The intervals for recording are 5 to 15 minutes, until at least two successive zeroes are obtained. The onset of drug action is taken as the time to reach 2 units of coolness intensity. The active compounds here, e.g, 1-7 produce cooling with 1 min after application. The duration of Dapa-compound action is defined as the offset time minus the onset time. The offset of drug action is defined here as the time when coolness intensity drops below 2, after previously surpassing 2 units.

Test compounds were applied to the skin of the forehead and zygomatic using cotton gauze (0.4 g, rectangular, 50 mm×60 mm; from CS-being, Daisan Cotton, Japan). The test compounds were used at a concentration of 20 mg/mL in distilled water. The results are summarized in the Table 4. From the data shown above, it can be seen that, among these compounds, 1-7 and 1-8 evoked cool/cold on zygomatic/forehead skin.

TABLE 4

Cooling properties of molecules applied to the zygomatic/forehead skin.

| Code | R | Carbon atoms | Onset (min) | Sensory Quality | Duration (hr) |
|---|---|---|---|---|---|
| 1-5 | 5 | 11 | ~1 | dynamic | 0.5 |
| 1-6 | 6 | 12 | ~1 | dynamic | 1.3 |
| 1-7 | 7 | 13 | ~1 | dynamic-icy | 3.2 |
| 1-8 | 8 | 14 | ~1 | cold-icy | 4.0 |
| 1-9 | 9 | 15 | ~2 | cool | 2.0 |
| 2-4 | 4 | 12 | ~1 | cool | 0.3 |
| 2-5 | 5 | 13 | ~1 | cool | 1.1 |
| 2-6 | 6 | 14 | ~2 | cold | 1.5 |
| 2-7 | 7 | 15 | ~2 | cold | 2.4 |
| 2-8 | 8 | 16 | 5 | cold | 5.6 |

Molecules of Table 1 and 2 activate TRPM8 ion channels. To determine if sensations of heat abstraction are accompanied by changes in tissue temperatures, 1-7 was applied to the forehead skin of subjects (N=5) (with a wipe and at a concentration of 20 mg/mL in distilled water) and skin temperatures recorded. The subjects noted the cooling effect of the 1-7 on the forehead skin which lasted for 30 to 45 min, but skin temperature is not affected 1-7. 1-7 produced refreshing and robust sensations of coolness which were invigorating to the test subjects: this effect was accompanied by a sense of freshness and dryness.

TABLE 5

Skin temperatures of human forehead after 1-7, 20 mg/mL.

| | Temperature (° C.) | |
|---|---|---|
| Time | Control | 1-7 |
| Before | 37.3 | 37.4 |
| 0 min | 37.2 | 37.4 |
| 15 min | 37.5 | 37.5 |
| 30 min | 37.1 | 37.1 |
| 45 min | 37.4 | 37.2 |
| 60 min | 37.0 | 37.1 |

Sebum is an oily substance secreted by the sebaceous gland. These glands, attached to hair follicles, are abundant on the face and scalp. Increased secretion of sebum, for example during teenage years, and associated with androgen stimulation is associated with acne. Sebum is also increased on an oily skin and in seborrheic dermatitis. Sebum secretion was measured here using a Sebumeter®, a standardized instrument based on a mat tape brought into contact with the skin, and then grease spot photometry [CK Electronic, Cologne, Germany].

Figure 2:
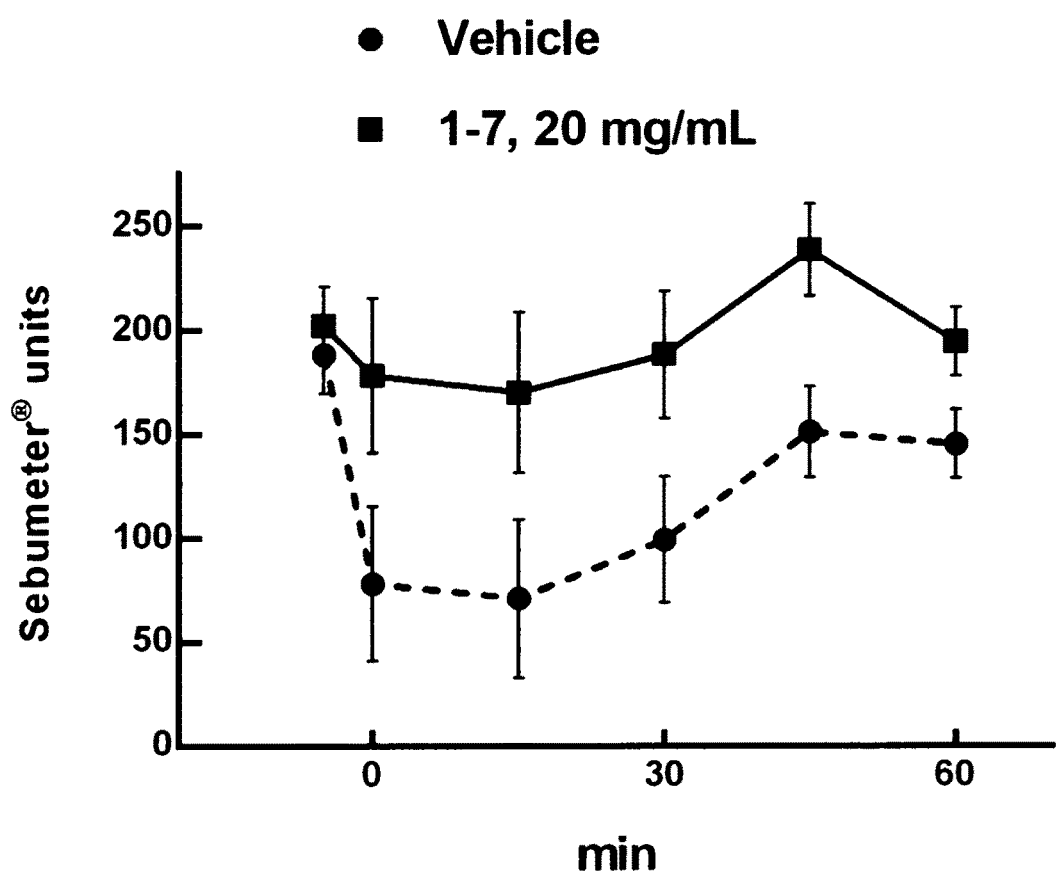
FIG. 2. is a graph showing sebum secretion after topical application of 1-7, 20 mg/mL, to forehead skin of volunteer subjects [N=4 or 5 per group]. Sebum levels were measured with a Sebumeter® [CK Electronic, Cologne, Germany].

In nine human subjects the baseline secretion of sebum was 188±19 μg/cm$^2$. After topical application with 1-7, 20 mg/mL, on the forehead, the sebum secretion was significantly decreased, as shown in FIG. 2. This pharmacological effect has not been previously observed with Dapa-compounds such as 1-7. This was a new and unexpected observation.

FIG. 2. is a graph showing sebum secretion after topical application of 1-7, 20 mg/mL, to forehead skin of volunteer subjects [N=4 or 5 per group]. Sebum levels were measured with a Sebumeter® [CK Electronic, Cologne, Germany].

Study 3. Effects of 1-7 and 1-8 on Sebocytes

The activities of 1-7 and 1-8 on an immortalized sebocyte cell line were examined in the laboratory of Prof Im Myung using methods previously described [Im et al. Epigallocatechin-3-gallate suppresses IGF-I-induced lipogenesis and cytokine expression in SZ95 sebocytes. J. Invest. Dermatol. 132, 2700-8 (2012)]. Proliferation of the sebocytes was measured using the MTT assay, by examination of micrographs of the cells in culture, and $^3$H-thymidine incorporation. The effects of the test agents on lipogenesis were further studied by Oil Red O staining and analysis of the lipid composition of the cells. Studies were also conducted on signaling pathways for lipogenesis [PPAR and SREBP-1, Trivedi et al. Peroxisome proliferator-activated receptors increase human sebum production. J. Invest. Dermatol. 126, 2002-9 (2006)].

The MTT assay is a colorimetric assay for cell viability. MTT [3-(4,5-dimethylthiazol-2-yl)-2-5-diphenyltetrazolium bromide], a yellow tetra-azole dye, is reduced to purple formazan in living cells by NADPH-dependent oxidoreductase enzymes. When the number of viable cells decreases the amount of enzymatic activity and purple color decreases and this can be measured with a spectrophotometer. When viable cells are incubated in the presence of 1-8 [0.1 mM], photomicrographs of the cell cultures also showed patchy empty spaces, confirming the loss of viable cells.

Figure 3:
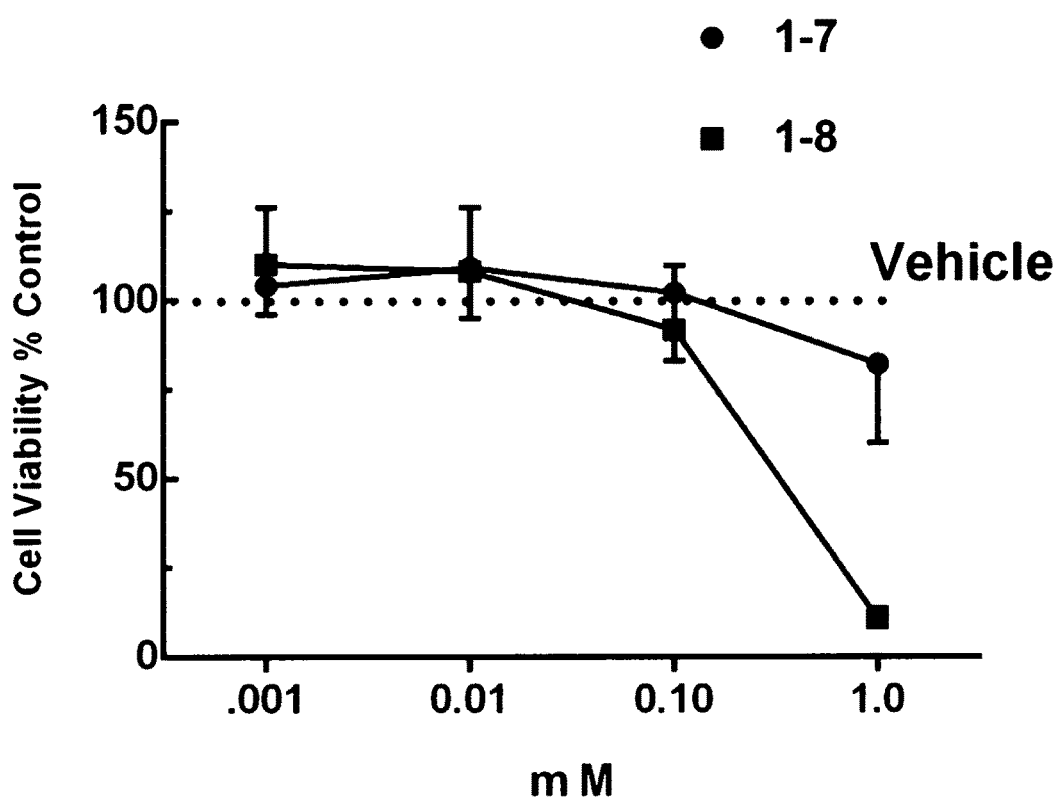
FIG. 3. is a graph showing sebocyte cell viability as % of controls measured by the MTT assay [ordinate] versus the concentration in mM of test substances [abscissa]. In the graph, 1-7 [circles] did not inhibit but 1-8 [squares] at 1 mM strongly inhibited sebocyte viability.

FIG. 3. is a graph showing sebocyte cell viability as % of controls measured by the MTT assay [ordinate] versus the concentration in mM of test substances [abscissa]. In the graph, 1-7 [circles] did not inhibit but 1-8 [squares] at 1 mM strongly inhibited sebocyte viability.

To determine if functional sebum production was affected by 1-8, sebocytes were stimulated with IGF-1, 50 ng/mL. IGF-1 is "insulin-growth factor" and is a protein that exerts hormone-like activity in increasing cell functions [Smith et al. IGF-1 induces SREBP-1 expression and lipogenesis in SEB-1 sebocytes via activation of the phosphoinositide 3-kinase/Akt pathway. J. Invest. Dermatol. 128, 1286-93 (2008)]. Oil Red 0 [Sudan Red 5B] is a diazo dye used for staining neutral triglycerides and lipids on cells. Study of the photomicrograph of sebocyte revealed that lipids are increased in cells after IGF-1, and this increase is inhibited in cells treated with 1-8 [0.1mM]. This inhibition if further confirmed by analytical measurements of lipids, using thin-layer chromatography and gas-chromatography. Squalene and wax esters, lipids that are specific to sebum [Picardo et al., 2009], were selectively decreased by 1-8. This drug action of 1-8 may be especially important for an anti-acne effect because it is thought that squalene peroxide is an instigator of ductal cell proliferation, an event that leads to the plugging of the hair follicle and the formation of comedones. The plugging of sebum drainage may then lead to bacterial invasion of the sebum, and the generation of irritants that lead to the inflammatory manifestations of acne [Cunliffe et al. 2004].

There are intracellular biochemical receptors and markers of sebocyte activation and sebum production. Peroxisome proliferator-activated receptors [PPAR] agonists increase sebum production in isolated sebocytes [Trivedi et al. (2006)]. This class of receptors is reduced after 1-8. Similarly, the sterol-response binding protein [SBEP-1] which is linked to lipogenesis in sebocytes, was reduced by 1-8. These effects were specific to the markers of sebum production, as cellular receptors such as TRPM8 and actin were not affected by 1-8.

This set of studies clearly shows that, at the cellular/sebocyte level, 1-8 is a potent inhibitor of sebocyte function at 0.1mM. These cellular effects were not seen 1-7, although this compound diminished sebum secretion on the forehead skin of volunteers. This is the first time that a 1-dialkyl-phosphorylalkane is shown to be a specific inhibitor of sebocyte function.

Study 4 Super-Potent Preferred Embodiments.

1-7 and 1-8 are sensory cooling agents on the skin and activators [agonists] of the TRPM8 ion channel protein. As can be seen in the Table 3 and in FIG. 1 and the data of Table 6, when various agonists were compared, there is no correlation between potency of TRPM8 activation and inhibitory effects on sebocyte function, so these two events are not related. The indicators used for direct comparison were sebocyte viability measured in the MTT assay and then the $^3$H-thymidine incorporation assay.

Figure 4:
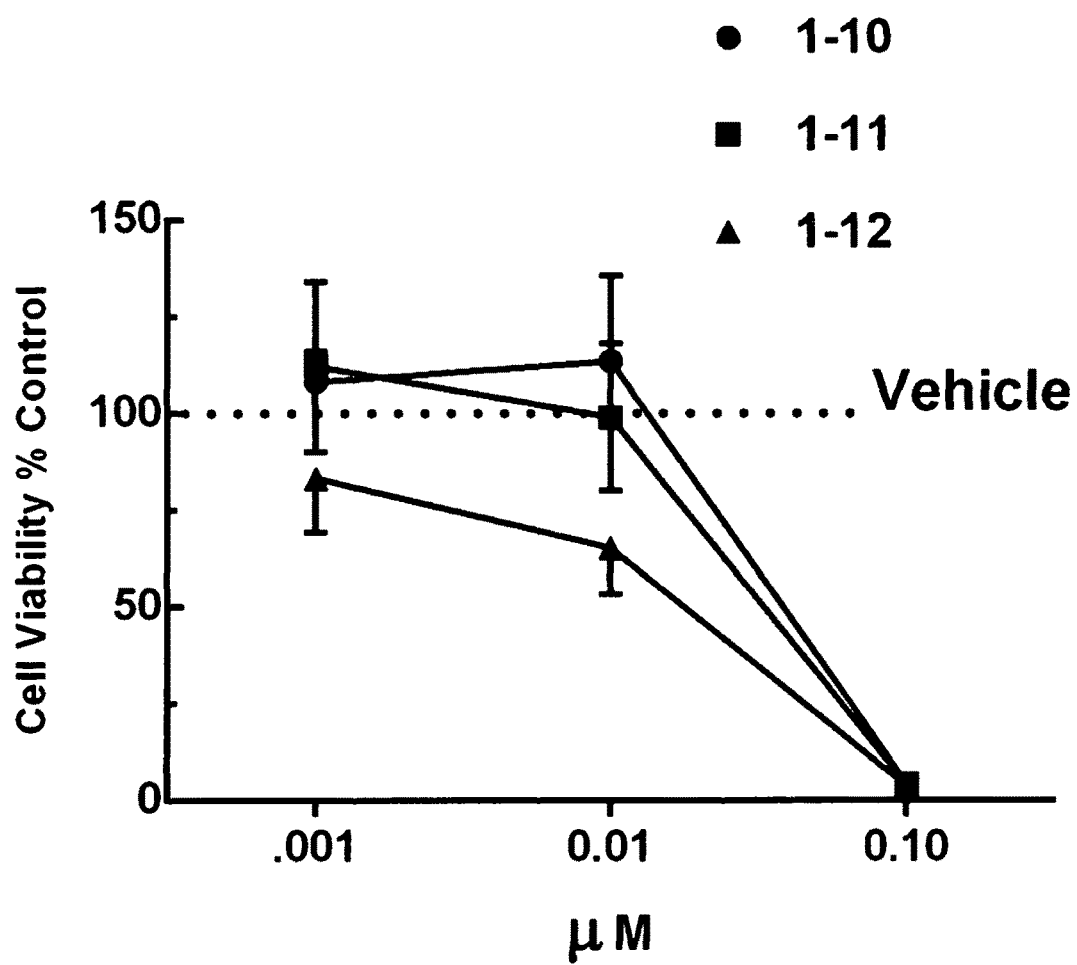
FIG. 4. is a graph showing sebocyte cell viability as % of controls measured by the MTT assay [ordinate] versus the concentration in µM of test substances [abscissa]. In the graph, all three test substances, 1-10, 1-11, and 1-12, strongly inhibited sebocyte viability at 0.10 µM.

Analysis of structurally related analogs of Dapa, showed that the compounds 1-10, 1-11, and 1-12 were most active to inhibit sebocyte viability. In FIG. 4, it can be seen that 1-10, 1-11 and 1-12 are 10,000x more active 1-8 in the MTT sebocyte assay. Also, 1-12, the most potent analog, was the only compound that clearly inhibited $^3$H-thymidine incorporation into sebocytes. 1-12 was fully effective at 0.01 µM, which is equivalent to 30 µg/mL. 1-12 was also effective at inhibiting IGF-1 stimulated production of squalene in the cultured sebocytes. The compounds 1-10, 1-11, and 1-12 were tested at three concentrations and the dose-response data for the MTT assay shown in FIG. 4.

FIG. 4. is a graph showing sebocyte cell viability as % of controls measured by the MTT assay [ordinate] versus the concentration in µM of test substances [abscissa]. In the graph, all three test substances, 1-10, 1-11, and 1-12, strongly inhibited sebocyte viability at 0.10 µM.

Figure 5:
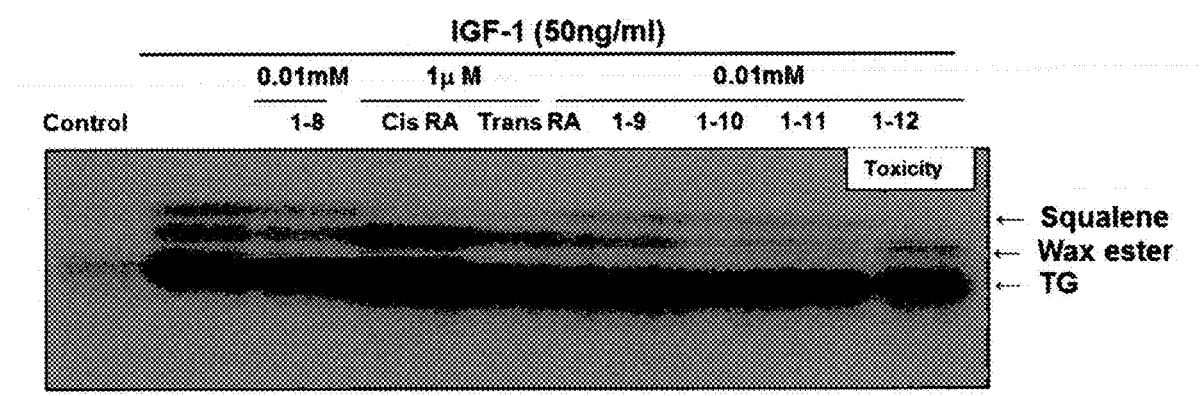
FIG. 5. shows a photo of a thin layer chromatography plate of lipids extracted from sebocytes that were incubated with various test substances. In the presence of insulin growth factor [IGF-1] lipids are increased, as measured by gel staining, and inhibited by cis- and trans- retinoic acid (RA). As can be seen in the photo, 1-10, 1-11, and especially 1-12 lowers the levels of squalene.

FIG. 5. shows a photo of a thin layer chromatography plate of lipids extracted from sebocytes that were incubated with various test substances. In the presence of insulin growth factor [IGF-1] lipids are increased, as measured by gel staining, and inhibited by cis- and trans-retinoic acid (RA). As can be seen in the photo, 1-10, 1-11, and especially 1-12 lowers the levels of squalene.

The potent inhibitory effects of 1-10, 1-11, and 1-12 on cellular growth are unexpected and novel. The range of cell types in which this drug action is manifested is still unknown, but the data clearly indicate that these compounds may be useful in proliferative dermatoses such as psoriasis, neurofibromatosis, necrosis lipoidica diabeticorum, and in manifestations of acne vulgaris. Furthermore, these compounds may be useful in the control and management of malignant, unrestrained, proliferation of somatic cells [cancerous lesions] and for the inhibition of lipid synthesis.

TABLE 6

Test substances on sebocyte viability, as measured by the MTT assay and $^3$H-thymidine uptake into cells.

| Code | Mol. Wt | MTT viability at 0.1 µm | $^3$H-thymidine uptake at 10 µM |
|---|---|---|---|
| 1-7 | 232 | NS, ≥100% | NS, ≥100% |
| 1-8 | 246 | ~60% | NS, ≥78% |
| 1-9 | 260 | ~60% | NS, ≥85% |
| 1-10 | 274 | ≤5% | NS, ≥100% |
| 1-11 | 288 | ≤5% | NS, ≥88% |
| 1-12 | 302 | ≤5% | ~40% |
| 2-5 | 232 | NS, ≥100% | NS, ≥98% |
| 2-6 | 246 | NS, ≥98% | NS, ≥100% |
| 2-7 | 260 | NS, ≥80% | NS, ≥85% |
| 2-8 | 274 | ~55% | NS, ≥90% |

Study 5. Amphiphilic Preferred Embodiments and Mechanisms of Action

The Dapa compounds examined here are "amphiphiles", i.e. they have hydrophilic and hydrophobic [lipophilic] properties at each end of the molecule. Many amphiphiles have "surfactant" or "surface-active" properties and are used in soaps and detergents. Surfactants confer cleansing action and lathering in shampoos and are designed to remove sebum from the hair shaft. Surfactants lower the surface tension between two phases, e.g. liquid-liquid, liquid-solid, and permit solid surfaces to be "wetted" or more easily coated with liquid. In addition to lowering surface tension, surfactants can form spherical aggregates [e.g. of 40 to 100 molecules] called "micelles" which can trap oil droplets into the center of the micelle and further enhance cleansing actions.

Figure 6:
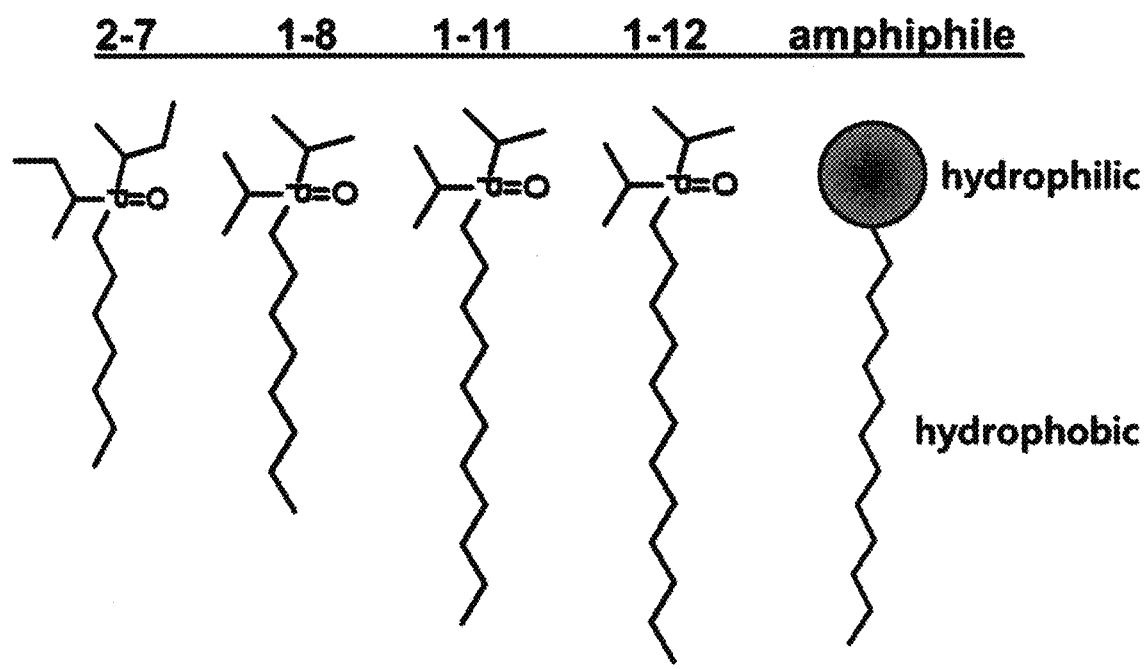
FIG. 6. shows the basic structure of an amphiphile with a hydrophilic "polar head" and a hydrophobic [lipophilic] "tail". The preferred embodiments 1-11 and 1-12 are amphiphiles. The disec-butyl groups [e.g. 2-7] cover the polar head more than the isopropyl groups [e.g. 1-8] with a resultant loss of bioactivity.

FIG. 6. shows the basic structure of an amphiphile with a hydrophilic "polar head" and a hydrophobic [lipophilic] "tail". The preferred embodiments 1-11 and 1-12 are amphiphiles. The disec-butyl groups [e.g. 2-7] covers the polar head more than the isopropyl groups [e.g. 1-8] and reduces hydrophilicity, with a resultant loss of bioactivity.

Figure 7:
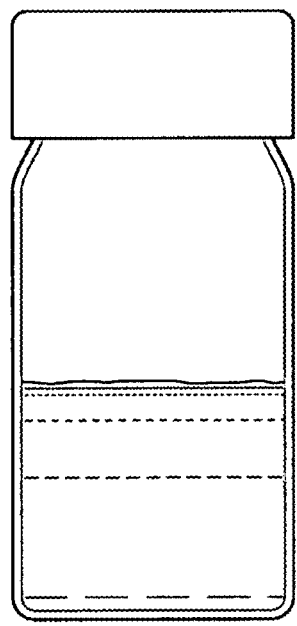
FIG. 7. shows an illustration of 1-11, 10 mg/mL in distilled water placed in a vial before [7A] and after manual shaking [7B]. The foaming seen in 7B is characteristic of a surface active agent or "surfactant" and is caused by an amphiphilic structure.
Figure 7:
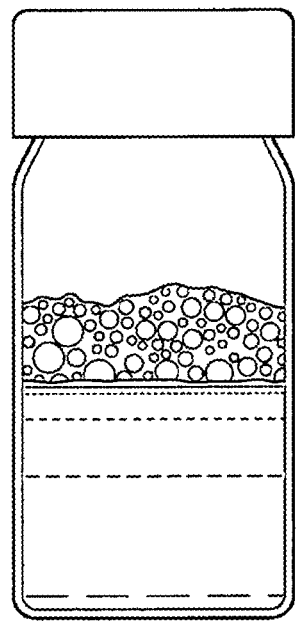

FIG. 7. shows an illustration of 1-11, 10 mg/mL in distilled water placed in a vial before [7A] and after manual shaking [7B]. The foaming seen in 7B is characteristic of a surface active agent or "surfactant" and is caused by an amphiphilic structure.

The ability of 1-11, a preferred embodiment, to lower surface tension of water is shown in FIG. 7. Plain water will not make bubbles because the water molecules are more strongly attracted to each other than to air. But when a surfactant is added, the surface tension of the liquid is reduced and it can wrap itself around air to form foam or soap bubbles. The foaming is enhanced when the liquid is shaken vigorously.

The preferred Dapa embodiments described herein can be categorized as non-ionic surfactants because the Dapa molecules do not have an electrical charge in solution. Standard surfactants used in shampoos are usually anionic [e.g. sodium lauryl sulfate]. Cationic surfactants include, for example, quaternary ammonium salts such as benzalkonium chloride which is used as an antimicrobial agent. Non-ionic surfactants include the ethoxylates [e.g. polysorbate 80 or sorbitan oleate] and propoxylates [e.g. PPG-10 cetyl ether]. The ability of dimethyl- and diethyl- phosphorylalkanes to act as surfactants and form micelles were recognized by physical chemists, [e.g. Lunkenheimer et al. (1987)] but the 1-dialkyl-phosphorylalkanes are not used for commercial applications as surfactants or detergents.

At this time, it is not yet clear if the preferred embodiments affect sebocyte viability by a surfactant action or by a selective and specific mechanism of action, e.g. interference with enzymatic activity, so the appropriate term is to call the Dapa embodiments amphiphiles and not surfactants. Lesnik et al. [Agents that cause enlargement of sebaceous glands in hairless mice. I. Topical Agents. Archives Dermatol. 284:100-105 (1992)] have examined the effects of cationic and anionic surfactants, solvents, and emulsifiers on the skin of hairless mice and found invariably that seboycte count is increased after chemical exposure: an effect that is opposite to what would be expected from the results shown here.

In FIG. 5, 1-12 is shown to potently reduce squalene production by sebocytes. Squalene is 30-carbon long-chain molecule important for lipid synthesis in skin cells. In human sebum the distribution of lipids is: glycerides 30-50%, free fatty acids 15-30%, wax esters 26-30%, squalene 12 to 20%, and cholesterol 3-6%. In young adults with acne, sebum production is increased on average by 59% and there is 2.2× fold increase in squalene content of the lipids [Pappas et al. Sebum analysis of individuals with and without acne. Dermato-Endocrinology 1:3, 157-164, June (2009)]. An agent that interferes with squalene physiology in sebocytes is likely to have profound inhibitory effects on sebum production. The structure of 1-12 resembles the amphiphilic properties of anionic fatty acids, so it is possible the mechanism of action of 1-12 in reducing sebocyte viability is inhibition of lipid synthesis.

Analysis of the structure-activity relationships of the preferred embodiments indicates that inhibitory potency on sebocytes is increased when the longest alkane chain is greater than or equal to 10 carbons. Note that 2-8 has more activity than 2-6 or 2-7 [Table 6], so even here extension of the alkane chain by one carbon increases potency. The isopropyl group is preferred to the sec-butyl, as illustrated by the absence of activities of 2-6 and 2-7 molecules on sebocyte viability whereas 1-9, which has the same number of carbons as 2-7 is active.

An increase in the number of carbons attached to the phosphorus atom could reduce the hydrophilic properties of the amphiphile. The anti-sebocyte activities of methyl, ethyl, and n-propyl analogs, singly or doubly substituted on the phosphorylalkane have yet to be studied. Such information could be directed to a general formula:

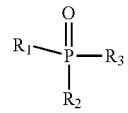

where $R_1$ and $R_2$=methyl, ethyl, isopropyl, or n-propyl, and $R_3$ is equal to alkyl side chain of ten to eighteen carbons.

Article of Manufacture

One embodiment of the invention is an article of manufacture that comprises a topical formulation of the invention in a suitable container with labeling and instructions for use. The container can be a manually-activated sprayer with a suitable small orifice size linked to a reservoir, a gel contained within a reservoir tube, or a towellette suitably sealed in a water-impermeable wrap.

Preferably, instructions are packaged with the formulations of the invention, for example, a pamphlet or package label. The labeling instructions explain how to administer topical formulations of the invention to the skin surfaces of the face, scalp, and trunk where pilosebaceous units are plentiful, in an amount and for a period of time sufficient to treat or reduce sebum secretion and seborrhea, and its signs and symptoms. The labeling instructions are an important aspect of the invention in that before a composition can be approved for any particular use, it must be approved for marketing by the United States Food and Drug Administration. Part of that process includes providing a label that will accompany the pharmaceutical composition that is ultimately sold. Preferably, the label includes the dosage and administration instructions, the topical formulation's composition, the clinical pharmacology, drug resistance, pharmacokinetics, absorption, bioavailability, and contraindications.

The invention claimed is:

1. A method for treating the skin of a mammal comprising: topically administering to a mammal in need thereof a composition, the composition having a compound dispersed in a dermatologically acceptable vehicle, wherein the compound administered has a therapeutic sebocyte cell activity and has the following structure:

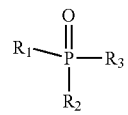

where R1 and R2 are isopropyl and R3 is alkyl chain of 10 to 18 carbons, wherein the mammal has acne, oily skin, or seborrheic dermatitis and the sebocvte cell activity of the administered compound is therapeutically effective in treating the acne, oily skin, or seborrheic dermatitis.

2. The method as in claim 1, wherein the compound is 1-diisopropylphosphoryldecane.

3. The method as in claim 1, wherein the compound is 1-diisopropylphosphorylundecane.

4. The method as in claim 1, wherein the compound is 1-diisopropylphosphoryldodecane.

5. The method as in claim 1, wherein the compound is present in the composition at a concentration of 0.001 to 5 mg/mL.

6. The method as in claim 1, wherein the dermatologically acceptable vehicle is an aqueous liquid, gel, lotion, cream, or ointment.

7. The method as in claim 1, wherein the composition includes water or a saline solution.

8. The method as in claim 1 wherein the composition is carried on an applicator, a swab, a wipe, a pad, or a towelette.

9. The method as in claim 1, wherein the composition is administered via a manually-activated sprayer or an airless bottle.

10. The method as in claim 1, wherein the composition is administered at an unit volume of 0.05 to 0.5 mL to the skin surface.

11. The method as in claim 1 wherein the administering is effective for enhancing the cosmetic appearance of a human subject with acne, oily skin, or seborrheic dermatitis.

12. The method as in claim 1 wherein the treating is for reducing proliferation of somatic cells in a mammal.

13. The method as in claim 1 wherein the treating is for reducing malignant, unrestrained, proliferation of somatic cells in a mammal.

14. The method as in claim 1 wherein the treating is for reducing synthesis of lipids in a mammal.

15. The method as in claim 1 wherein the treating is for reducing sebum secretion.

\* \* \* \* \*